United States Patent
Houdek et al.

[11] Patent Number: 5,107,839
[45] Date of Patent: Apr. 28, 1992

[54] COMPUTER CONTROLLED STEREOTAXIC RADIOTHERAPY SYSTEM AND METHOD

[75] Inventors: Pavel V. Houdek, 2121 N. Bayshore Dr., Apt. 1112, Miami, Fla. 33137; James G. Schwade, Miami, Fla.; Howard J. Landy, Miami, Fla.; Murray S. Ginsberg, Miami, Fla.

[73] Assignee: Pavel V. Houdek, Miami, Fla.

[21] Appl. No.: 519,184

[22] Filed: May 4, 1990

[51] Int. Cl.$^5$ .................................... A61B 6/03
[52] U.S. Cl. ...................... 128/653.1; 606/130; 600/1
[58] Field of Search ............ 128/653 R; 606/130; 378/163, 205, 207; 364/413.26; 250/360.07

[56] References Cited

U.S. PATENT DOCUMENTS

| | | |
|---|---|---|
| D. 288,368 | 2/1987 | Van Buren et al. |
| 4,223,228 | 9/1980 | Kaplan .................... 378/205 |
| 4,256,112 | 3/1981 | Kopf et al. |
| 4,262,306 | 4/1981 | Renner .................... 600/130 |
| 4,341,220 | 7/1982 | Perry |
| 4,465,069 | 8/1984 | Barbier et al. |
| 4,475,550 | 10/1984 | Bremer et al. |
| 4,583,537 | 4/1986 | Derenchinsky et al. ........ 606/130 |
| 4,602,622 | 7/1986 | Bar et al. |
| 4,608,977 | 9/1986 | Brown |
| 4,612,930 | 4/1986 | Bremer .................... 606/130 |
| 4,617,925 | 10/1986 | Laitinen |
| 4,618,978 | 10/1986 | Corman .................... 606/130 |
| 4,638,798 | 1/1987 | Shelden et al. |
| 4,706,665 | 11/1987 | Gouda |
| 4,791,934 | 12/1988 | Brunnett |
| 4,793,355 | 12/1988 | Crum et al. ............... 128/653 R |
| 4,805,615 | 2/1989 | Carol |
| 4,841,965 | 6/1989 | Jacobs .................... 606/130 |
| 4,951,653 | 8/1990 | Fry et al. ................ 128/653 R |

OTHER PUBLICATIONS

Medical Physics, vol. 10, No. 3, *Dosimetry of small radiation fields for 10-MV x rays*, Pavel V. Houdek et al., May/Jun. 1983.

Medical Physics, *Stereotaxic radiotherapy technique for small intracranial lesions* Pavel V. Houdek et al., Jul.-/Aug. 1985.

Applied Neurophysiology, vol. 46 "A Multipurpose CT-Guided Stereotactic Instrument of Simple Design", Van Buren et al. pp. 211-216 (1983).

*Primary Examiner*—Ruth S. Smith
*Attorney, Agent, or Firm*—Dickstein, Shapiro & Morin

[57] ABSTRACT

A computer controlled stereotoxic radiotherapy system is disclosed which facilitates a precise localization and subsequent irradiation of small intracranial tumors. The system permits the accurate integration of the diagnostic and therapeutic procedures utilized in connection with intracranial tumors, including precise determination of space coordinates of the tumor and the repetitive repositioning of the patients's head in space within a scanner and/or accelerator coordinate system. The system is uniquely designed for fractionated repetitive radiotherapy but may be used in other medical fields such as surgery and radiology.

18 Claims, 4 Drawing Sheets

A-A'

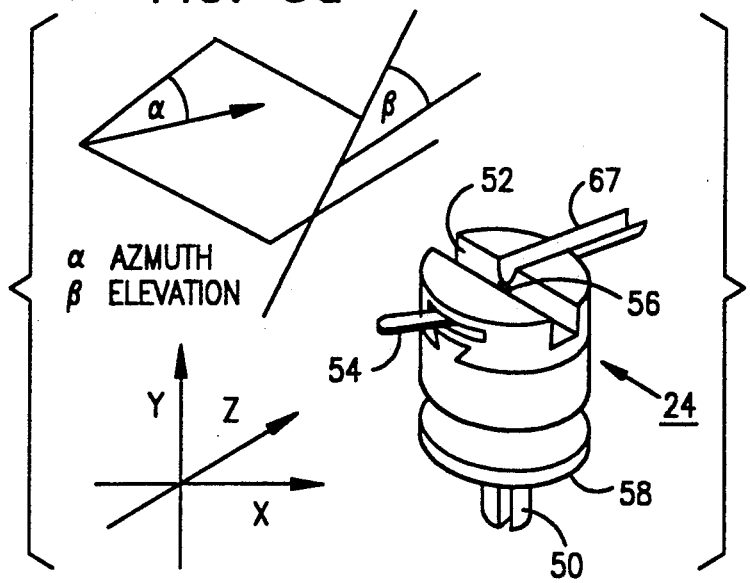
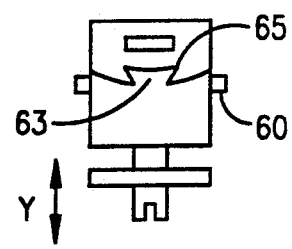
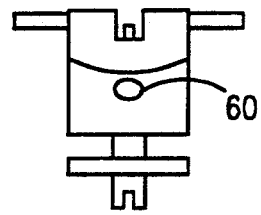
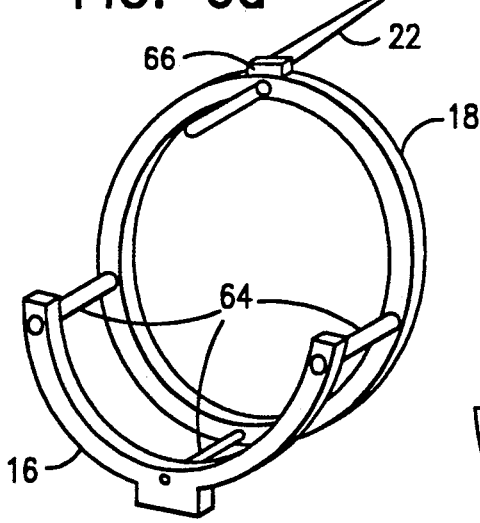
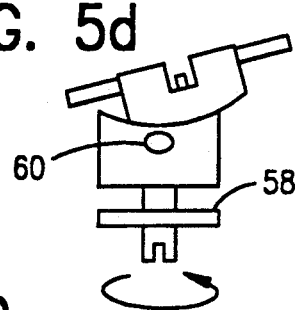
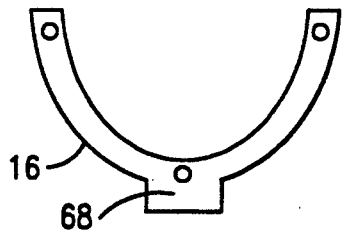
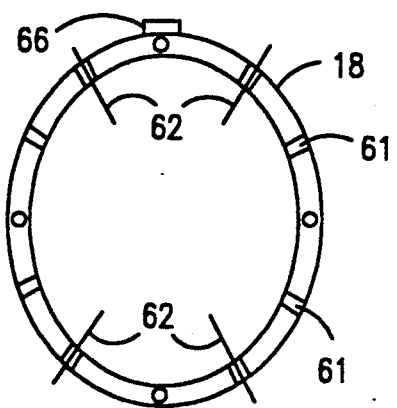
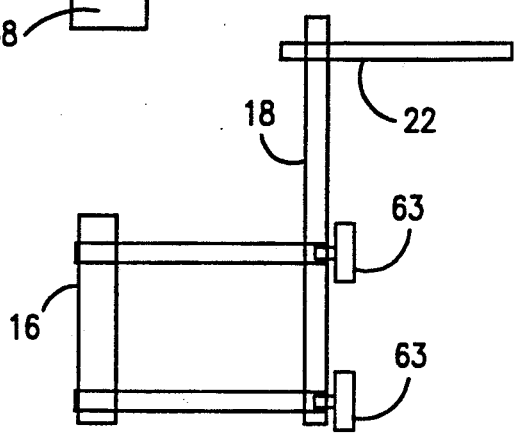

COMPUTER CONTROLLED STEREOTAXIC RADIOTHERAPY SYSTEM AND METHOD

BACKGROUND OF THE INVENTION

The present invention relates generally to the diagnosis and treatment of patients having tumors or lesions. More particularly, the present invention relates to a method of and system for locating and treating such tumors or lesions in which the same three-dimensional coordinate system used in diagnosing the location of the tumors or lesions is used to provide treatment for those tumors or lesions, by use of a computer and a stereotaxic ring.

Although a brain lesion as small as 2-3 millimeters can be localized on a computed tomography (CT) or magnetic resonance (MR) scanner, it cannot be treated with a correspondingly small radiation field(s) because the geometrical error associated with the information transfer from scanner to a computer to an accelerator and then to the patient is greater than the dimensions of the lesion itself. Thus, the ability to conduct precision radiotherapy using, for example, x-rays, is determined by the overall accuracy of the whole radiation therapy process, and not by the precision achieved in the individual diagnostic or therapeutic procedures.

While in the last fifteen years new technology has been introduced for nearly every procedure utilized in the diagnosis and treatment of brain lesions (for example, CT and MR scanners, treatment planning computers, compact linear accelerators, etc.), no system and/or equipment has been offered or is available for integrating the radiotherapy process. Consequently, the overall precision of the process has not yet improved to the extent made possible by present knowledge and technology.

This application discloses a computer controlled stereotaxic radiotherapy system which integrates, using a patient halo or headpiece, the diagnosis, treatment planning, and subsequent repetitive radiotherapy treatment for treating such lesions.

Stereotactic devices for use in aiding treatment of lesions are known. Examples of such stereotactic apparatus include U.S. Pat. No. 4,638,798 to Shelden et al.; U.S. Pat. No. 4,617,925 to Laitinen; U.S. Pat. No. 4,608,977 to Brown; U.S. Pat. No. 4,602,622 to Bar et al.; U.S. Pat. No. 4,465,069 to Barbier et al.; U.S. Pat. No. 4,341,220 to Perry; U.S. Pat. No. 4,256,112 to Kopf; U.S. Pat. No. 4,805,615 to Carol; U.S. Pat. No. 4,791,934 to Brunnett; U.S. Pat. No. 4,706,665 to Gouda; U.S. Pat. No. 4,475,550 to Bremer et al. and U.S. Pat. No. Des. 288,368 to Van Buren et al.

While some of the above-referenced patents disclose utilizing a computer to analyze and determine the coordinates of a lesion with reference to a ring or halo attached to the patient's head during diagnosis, such as the Shelden et al. and Gouda patents, none of those references are concerned with a computer controlled radiotherapy system which utilizes the coordinates developed from a CT or MR scanner. Not until applicants' invention was a system developed which integrates, under computer control, the processing of the coordinates locating the lesion during diagnosis and the subsequent processing and utilization of those coordinates by the treatment apparatus.

SUMMARY AND OBJECTS OF THE INVENTION

In view of the foregoing, it should be apparent that there still exists a need in the art for a method of and system for providing for the treatment for intracranial lesions or other tumors in which the diagnostic and treatment devices are integrated such that the coordinates of the lesion to be treated are provided to the treatment device in an accurate and direct manner. It is, therefore, a primary object of this invention to provide a method of and apparatus for integrating the diagnostic and treatment devices and procedures used in connection with the diagnosis and treatment of lesions in such manner that the treatment coordinates are automatically developed or computed as a result of the diagnostic coordinates of the lesion to be treated.

More particularly, it is an object of this invention to provide a system for locating and treating lesions as aforesaid which utilizes simple and reliable electronic circuitry which provides quick and accurate treatment coordinates as a result of the lesion coordinates computed from the scans obtained with the diagnostic apparatus.

Still more particularly, it is an object of this invention to provide a lesion treatment system in which the treatment coordinates are integrated with the diagnostic coordinates by means of a headpiece attached to the head of the patient and a base assembly attached to the treatment couches of both the diagnostic equipment and the treatment equipment.

Another object of the present invention is to provide a reliable and relatively inexpensive computer controlled stereotaxic radiotherapy system for use in treating lesions.

Briefly described, these and other objects of the invention are accomplished in accordance with the system aspects by providing a common mechanical system, (stereotaxic guide), which includes three major parts: a halo attached to the patient's head, a base unit attached to the treatment couches of both the diagnostic equipment and the treatment equipment and a stereotaxic cage. The mechanical equipment is used to integrate the lesion coordinates determined by the diagnostic equipment with those used by the treatment equipment to treat the lesion.

The halo is attached to the patient's cranium with skin piercing screws in a known manner and, is used in combination with the base assembly attached to the treatment couches of the respective diagnostic and treatment devices. The stereotaxic phantom cage, which fits over the halo, is secured to the base unit and allows the coordinates of the lesion, as well as other points of interest, (e.g. magnetic field sensor phantom), to be determined in the patient coordinate system. The stereotaxic guide also permits a subsequent transfer of the coordinates from the patient's coordinate system into the coordinate system of the diagnostic device, treatment planning computer, treatment equipment and the control computer.

The method of the present invention is carried out by first securing the halo to the head of the patient and then securing the halo to the base assembly portion of the mechanical system which is itself secured to the treatment couch of the diagnostic equipment. The stereotaxic cage is then placed over the halo and secured to the base unit. A magnetic probe phantom or field sensor is secured to the halo and the diagnostic device is then used to obtain a series of diagnostic scans covering the entire volume of interest, including the lesion and the probe. The stereotaxic coordinates of the lesion and the field sensor are determined from the obtained scans using the contrast points provided by the stereotaxic phantom cage on the scans. The relation of the patient and scanner coordinates systems (origin, orientation) is also established. This relation may be needed if additional scans are required later—it permits precise patient repositioning within the diagnostic machine coordinate system.

The scans, stereotaxic coordinates and patient and scanner coordinate systems relation are then transferred to the treatment planning computer. That planning computer is then used to develop an optimal treatment strategy (radiation beam modality and energy, field size, treatment technique, fractionation, etc.) and finally to compute the distribution of the dose (energy absorbed) throughout the volume of interest and in particular within the lesion itself.

The treatment plan is computed in the patient coordinate system which is determined by the stereotaxic guide. The patient is ten moved to a treatment device and is secured, by means of the same halo and same base unit, to the couch of the treatment machine in the same manner as previously secured to the couch of the diagnostic equipment. A magnetic field sensor is secured into the patient halo and a magnetic field source is attached to the treatment machine. Both the sensor and source are then connected through a three dimensional converter to a control computer. The probe senses (digitizes) the magnetic field generated by the source in real time and thus the probe's coordinates (x, y, z, azimuth, elevation, and roll) are continuously displayed on the control computer in the treatment room.

The coordinate system of the control computer is then established by positioning the field sensor into the treatment device isocenter (the point in space around which the radiation source rotates) and assigning the isocenter as the origin. The orientation of the control computer and treatment device coordinate systems is then adjusted to coincide. Since the stereotaxic coordinates of the lesion and the probe are already known, the patient is then setup in space in a manner so that the control computer reads the lesion coordinates as previously determined but now transferred into the coordinate system of the treatment machine.

Verification films are then taken and the six coordinates are recorded. The control computer, which may be portable, is transferred to the outside of the room and is then used to monitor patient motion during treatment. Patient setup for subsequent treatments is done in the same manner using the six stereotaxic coordinates and the control computer. By means of providing information about patient and machine relative positions, an accidental collision during treatment may be avoided.

Since there is no need to remove the halo from the head of the patient during treatment, the halo typically remains on the patient's head during the entire series of treatments (several weeks) and, together with the control computer, allows the accurate alignment of the radiation beam of the treatment machine to the desired lesion treatment coordinates.

The stereotaxic guide, through its stereotaxic phantom cage and halo attached to the cranium (bone fixation), determines the patient coordinate system (CS) including the origin and orientation. From the CT or MR scans, the stereotaxic coordinates of the lesion and field sensor are determined in the patient CS. At the same time, the relation between the patient's and diagnostic unit coordinate systems is established. The data, meaning the scans, the lesion and probe coordinates and relation between patient CS and diagnostic machine CS are transferred into the treatment planning computer. The treatment plan/strategy is computed in the patient CS.

The patient is moved into the treatment room with halo and field probe attached and a low frequency magnetic field is generated by the source secured to the treatment machine. Both the probe and the source are connected via a converter to the control computer. The probe digitizes the 3D space field in real-time. The probe (and consequently the halo, and consequently the patient and hence the lesion) position (x, y, z) and space orientation (azimuth, elevation, roll) are instantly displayed on the control computer in the treatment room. The coordinate system of the control computer, that is, the origin and orientation of the magnetic field CS, is established in such a manner, that the origin is set to be the treatment machine isocenter and its orientation is made to coordinate with the treatment machine CS.

The stereotaxic coordinates of the lesion and the probe are then recomputed (transferred) from the patient CS into the control computer (and hence the treatment machine) coordinate system. The patient is then manipulated in space until the control computer displays the transferred stereotaxic coordinates of the lesion. Subsequent patient setup for additional treatments is done in the same manner.

During the actual treatment, the control portable computer is placed outside of the room and is used to monitor patient motion during the treatment session. If the motion is excessive, the treatment can be interrupted. Furthermore, the control computer provides continuous information concerning the relative position of the patient (field probe) and treatment machine (field source). That data may be used to halt the machine motion if that motion would result in a machine-patient collision. It should be noted that for the majority of patients, the treatment technique of choice is a "moving beam therapy" meaning that during the treatment the treatment machine rotates around the lesion (patient).

If any re-planning or additional scanning needs to be done—as long as the patient has the halo attached—the patient can be precisely repositioned in the diagnostic machine CS because the relation between the patient and diagnostic machine coordinate systems is already known.

With these and other objects, advantages and features of the invention that may become hereinafter apparent, the nature of the invention may be more clearly understood by reference to the following detailed description of the invention, the appended claims, and to the several drawings attached herein.

BRIEF DESCRIPTION OF THE DRAWINGS

FIG. 3d is a drawing of the base support taken through the lines A—A' of FIG. 3a;

FIG. 5a is a drawing of the perspective view of the gyro assembly used with the present invention;

FIG. 5b is a drawing of the front view of the gyro assembly used with the present invention;

FIG. 5c is a drawing of a side view of the gyro assembly used with the present invention; and FIG. 5d is a drawing of a side view of the gyro assembly used with the present invention showing the gyro elevation and azimuth motions;

FIG. 6a is drawing of a perspective view of the halo assembly used with the present invention;

FIG. 6b is a drawing of the front view of the halo support which forms part of the halo assembly shown in FIG. 6a;

FIG. 6c is a drawing of a front view of the halo which forms part of the halo assembly shown in FIG. 6a; and FIG. 6d is a drawing of the side view of the halo assembly shown in FIG. 6a.

FIG. 7b is a drawing of the front view of the phantom or cage shown in FIG. 7a; and FIG. 7c is a drawing of the side view of the phantom or cage shown in FIG. 7a.

DETAILED DESCRIPTION OF THE PREFERRED EMBODIMENT

Figure 1:
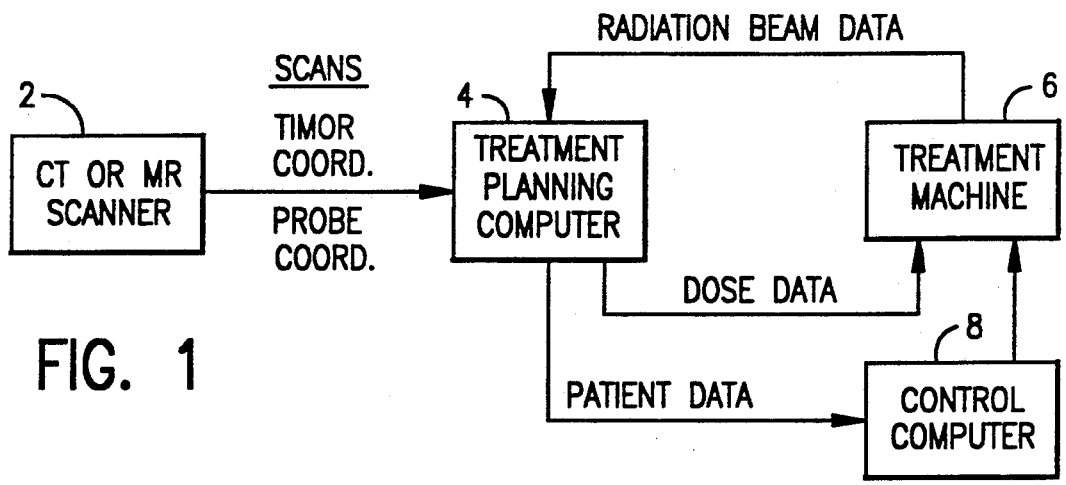
FIG. 1 is an electrical block diagram showing some of the electronic equipment utilized with the apparatus of the present invention.

Referring now in detail to the drawings wherein like parts are designated by like reference numerals throughout, there is illustrated in FIG. 1 a schematic block diagram of a portion of the computer system utilized with the computer controlled stereotaxic radiotherapy system of the present invention. A CT scanner 2, such as a General Electric Model 8800 or 9800, is used together with the mechanical assemblies of the present invention, as shown, for example, in FIG. 2 and as will be described later herein, to produce the scans and associated tumor coordinates of a patient having, for example, a brain lesion. The CT scanner 2 may also be used in conjunction with a three-dimensional digitizer device and accompanying software, such as the 3Space Three-Dimensional Digitizer available from Polhemus Navigation Sciences Division of McDonald Douglas Electronics Company, Colchester, Vt. 05446.

The tumor and probe coordinates are transferred to the treatment planning computer 4, which may be, for example, an IBM-PC or AT class or one of the DEC-VAX family of computers, where the treatment plan is designed, using treatment planning software, for example, General Electric Target or Therplan software by Theratronix. Further, the treatment computer 4 has in its memory the radiation beam data from the relevant treatment device 6 (shown in FIG. 8).

The three-dimensional digitizer utilizes magnetic transducing technology to precisely measure the x, y and z position of the tumor, as will be described later in more detail, as well as the three orientation angles of the digitizer stylus or probe itself. The 3Space Three-Dimensional Digitizer is provided with a system electronics unit which includes the hardware and software necessary to control the digitizer elements and to interface with the host computer, such as the control computer 8, utilized in the present invention, a probe or stylus that houses a magnetic-field sensor which is used to designate the point to be digitized, such as the isocenter of the treatment machine, and a low-frequency magnetic field device which is mounted in the vicinity of the probe, for example, to the treatment machine 6 to which the probe is referenced in space.

Figure 2:
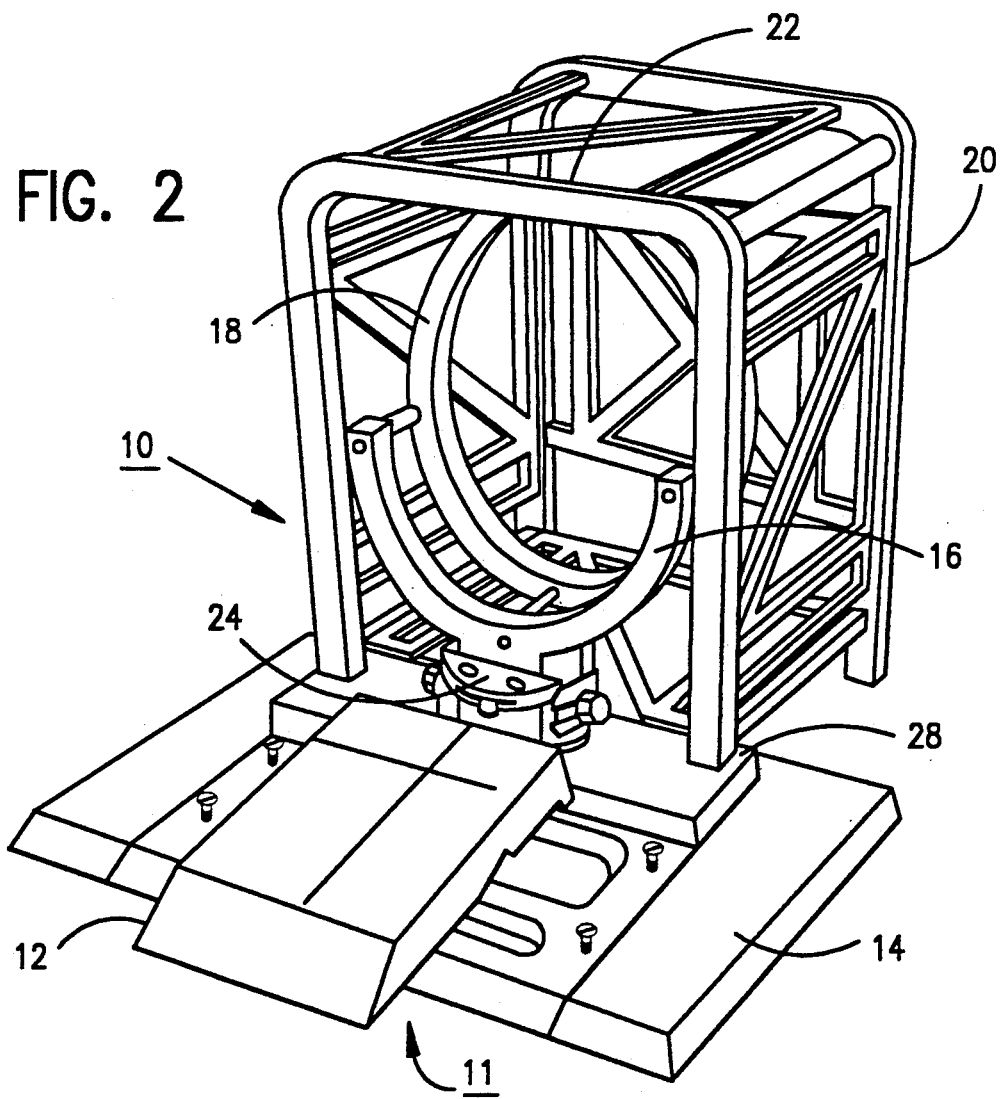
FIG. 2 is a perspective drawing of the mechanical system of the present invention.

Referring now to FIG. 2, there is shown the mechanical assembly 10 utilized as part of the inventive computer controlled stereotaxic radiotherapy system. The mechanical assembly 10 includes a base assembly 11 formed of a base 12 which is movably secured to a base support 14. Attached to the rear portion 28 of the base 12 is a gyro assembly mounting element 24 to which the halo support 16 and attached halo 18 are releasably mounted. Removably attached to the rear 28 of the base 12 is a stereotaxic coordinates phantom or cage 20 which contains a different contrast material, depending upon whether the cage or phantom 20 is used with a CT scanner or a magnetic resonance imaging (MRI) machine. A field sensor or probe 22, such as that previously described as part of the 3Space Three-Dimensional Digitizer system is removably mounted to the stereotaxic coordinates phantom or cage 20. A probe phantom with no metal coils inside is used in MR scanner.

Referring now to FIGS. 3a–3d, there are shown drawings of the base support 14 for use with the present invention. The base support 14 is attached to the treatment couches of both the CT scanner 2 and the treatment device 6, which may be a linear accelerator such as the Toshiba Model LMR13 or Varian Model 2500C. By utilizing the same base support 14 secured in the same position on the treatment couches of both the CT scanner and linear accelerator, the system of the present invention is able to automatically correlate the precise coordinates of the lesion. It is also necessary to the success of the present invention, of course, that the halo 18 together with the halo support 16 be affixed to the portion of the patient's body to be treated, such as the head, and to remain fixed in that same position throughout the course of treatment to be administered to the patient. Skin piercing screws with pins which are secured into the bone (cranium) are used.

Figure 3A:
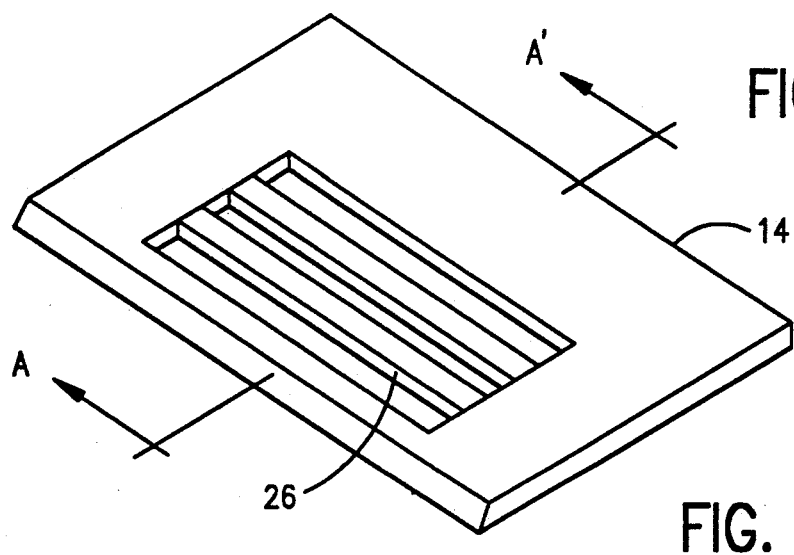
FIG. 3a is a perspective drawing of the base support of the present invention.
Figure 3B:
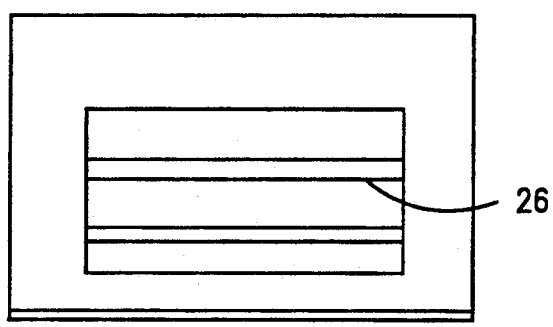
FIG. 3b is a drawing of the top view of the base support of the present invention.
Figure 3C:
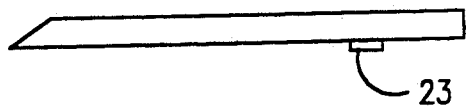
FIG. 3c is a side drawing of the side view of the base support of the present invention.
Figure 3D:
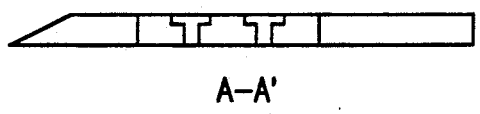

The base support 14 is fixed to the couch of the CT scanner 2 and to the treatment couch 80 of the treatment machine 6 by any suitable means, such as by the peg 23 with interlocking mechanism (not shown) shown in FIG. 3c. The base support 14 is provided with a plurality of bar-like elements 26 to which the base 12 may be movably affixed, in order to provide for movement in the transverse direction of the treatment couch. In that manner, the couch can always be centrally located and collisions between the moving accelerator 6 and stationary couch 80 can be avoided—at least in the base arc.

Although only two bar-like elements 26 are shown, it is of course well known in the art that any type and number of elements may be utilized to accomplish the alignment process described above; the only requirements being that the base 12 be able to be movably attached to the base support 14 in a simple and easy to accomplish manner. It should also be noted that the entire base assembly 11 may be constructed from any non-magnetic material, such as DELRIN (acetal resin) available from COMCO Corporation.

Figure 4A:
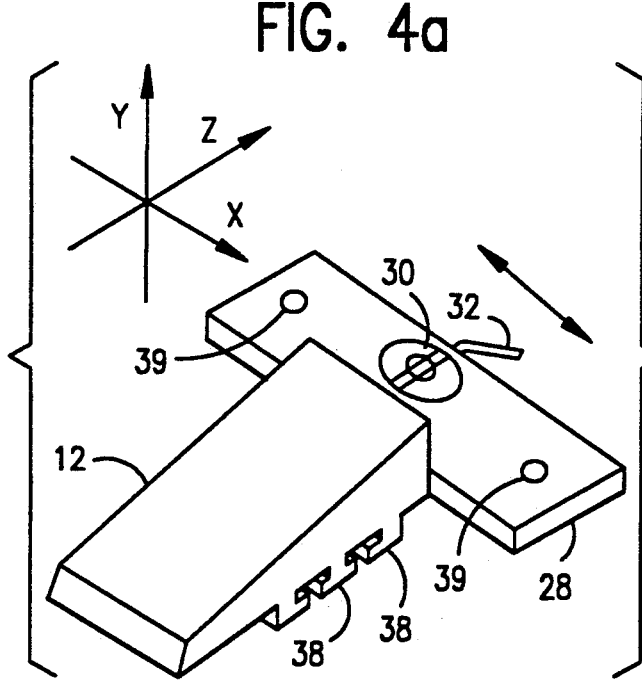
FIG. 4a is a drawing of a perspective view of the base used with the present invention.
Figure 4B:
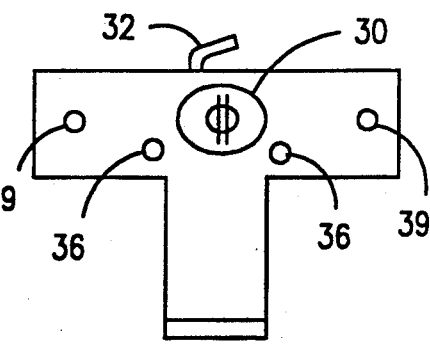
FIG. 4b is a drawing of a top view of the base used with the present invention.
Figure 4C:
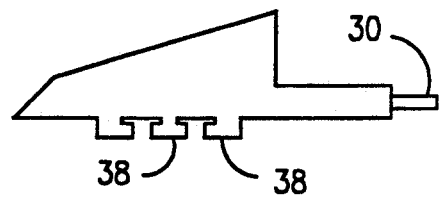
FIG. 4c is a drawing of the side view of the base used with the present invention.
Figure 7A:
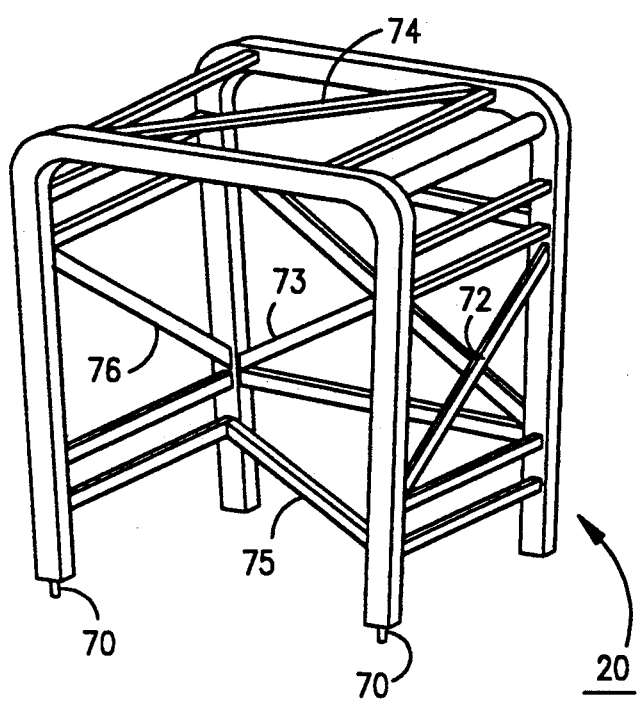
FIG. 7a is a drawing of a perspective view of the stereotaxic coordinates phantom or cage used with the mechanical system of the present invention.
Figure 7B:
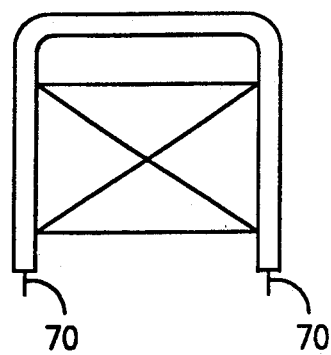
Figure 7C:
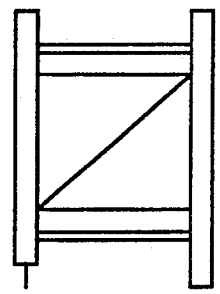

FIGS. 4a-4c show details of the base 12 which may be of a T-shaped configuration. The crosspiece 28 of the base 12 may contain a locking member 30 having a locking lever 32 to receive the gyro assembly 24. A plurality of lock members 36, of any suitable type, may be utilized to secure the base 12 relative to the base support 14 and to allow movement between the base 12 and the base support 14 in a direction perpendicular to the longitudinal axis of the treatment couch 80. As shown in FIGS. 4a and 4c, a plurality of fingers 38 are utilized to secure the base 12 to the base support 14 and at the same time to provide for the positioning of the base 12 with respect to the treatment sides of the couch 80. The crosspiece portion 28 of the T-shaped base 12 also includes a pair of locator elements 39 which may be, for example, pins or holes, for precisely locating the stereotaxic coordinate phantom 20 to the base 12.

FIGS. 5a-5d show details of the gyro assembly 24 which is secured to the base 12 by means of the gyro lock 30. The gyro 24 includes a shaft 50 which is secured within the gyro lock 30. As shown in FIGS. 5a-5d, the shaft 50 may be partially split such that it is more securely removably attached to the base 12 by means of the gyro lock 30 and locking lever 32 (shown in FIGS. 4a-4b). The purpose of the gyro lock 30 is to provide rotation of the halo 18 and halo support 16, which is secured to the top of the gyro assembly 24 by means of the slot 52 and halo lock 54 about the y axis, as well as to provide adjustment of the attached halo 18 in the azimuth and elevation angles. In order to more securely affix the halo support 16 and attached halo 18 to the gyro assembly 24, a halo locating pin 56 is provided within the slot 52 located at the top of the gyro assembly 24. A gyro ring 58 is provided with which to easily rotate the gyro assembly 24 about the y axis of the base 12, which is also the y axis of the treatment couch 80. The gyro ring 58 also facilitates gyro motion in the y direction.

As discussed above, the gyro assembly 24 also provides or elevation motion. A tongue 63 and groove 65 structure as shown in FIG. 5b is provided and is secured by means of an elevation motion lock 60. When the elevation motion lock 60 is released, the elevation angle of the gyro assembly 24 may be modified and then a new elevation angle secured, again by means of the elevation motion lock 60. A modification of the gyro elevation angle is shown in FIG. 5d.

The gyro assembly 24 also includes a supporting member 67 which provides additional support to the halo support 16 inserted into the slot 52 after being aligned with the halo locating pin 56 contained at the top of the gyro assembly 24. The gyro assembly 24, as well as the halo 18 and halo support 16 and base assembly 11, may all be preferably formed from non-magnetic material. Such material includes plastic, such as DELRIN (acetal resin) with titanium hardware.

FIGS. 6a-6d show the halo 18 and halo support 16. As shown in FIG. 6b, the halo support 16 is of a generally U-shaped configuration. At the base of the halo support 16 is a tab 68 which is used to secure to the halo support to the gyro assembly 24.

As shown in FIG. 6c, the halo 18 is formed as an elongated circle, for use in treating a cranial lesion. Obviously, the halo may be of a somewhat modified shape if the system of the present invention is used, for example, to treat a patient's prostate. The halo 18 is formed as a single ring of non-magnetic material, such as DELRIN (acetal resin) which contains titanium inserts 61. The halo is secured to the skull of a patient to be treated by means of titanium skin piercing screws 62. Different inserts may be utilized for different patients as determined, e.g., by the position of a previous craniotomy, etc. The halo itself can be either of a standard size or a custom size if required, e.g., a pediatric halo.

The halo 18 is attached to the patient after a local anesthesia is injected into the skull of the patient in the places where the four screws 62 will be attached. Once the halo 18 is applied, and the titanium screws 62 tightened, only the tip of each screw 62 engages in the skull, with about 7 pounds per square inch of force. Since the halo 18 is preferably formed of a plastic material with titanium screws and inserts, it is relatively light and does not provide excessive strain on the patient's head and neck.

As shown in FIGS. 6a, 6c and 6d, a probe 22 for the three-dimensional digitizer is removably fixably secured at one end of the halo 18, preferably the top end of the halo 18 nearest the patient's face, by means of a halo lock 66. The halo 18 is secured to the halo support 16 by a plurality of plastic rods 64 and plastic screws 63 which serve to space the halo 18 away from the halo support 16, while at the same time maintaining a parallel relationship between the halo support 16 and the halo 18.

FIGS. 7a-7d show the stereotaxic coordinates phantom 20 for use with the present invention. The phantom 20 may be provided with two pins 70 which are inserted into the locator elements 39 contained in the crosspiece 28 of the base 12.

The purpose of the stereotaxic coordinates phantom 20 is to provide reference points with respect to the isocenter of the lesion to be treated that are produced during diagnosis using, for example, a CT scanner or an MRI machine. That function is accomplished by means of a contrast material contained within the Z-shaped elements 72, 76, 74, 73 and 75 affixed respectively to the sides, the top, the back and bottom of the phantom or cage 20. There are 2 identical stereotaxic phantoms; one for CT and one for MRI procedure. The only difference between them is the type of contrast material used, e.g., aluminum wire for CT and $CuSO_4$ wire for MRI. The phantom 20 is used only during the diagnostic process, and is not needed during the treatment phase.

Figure 8:
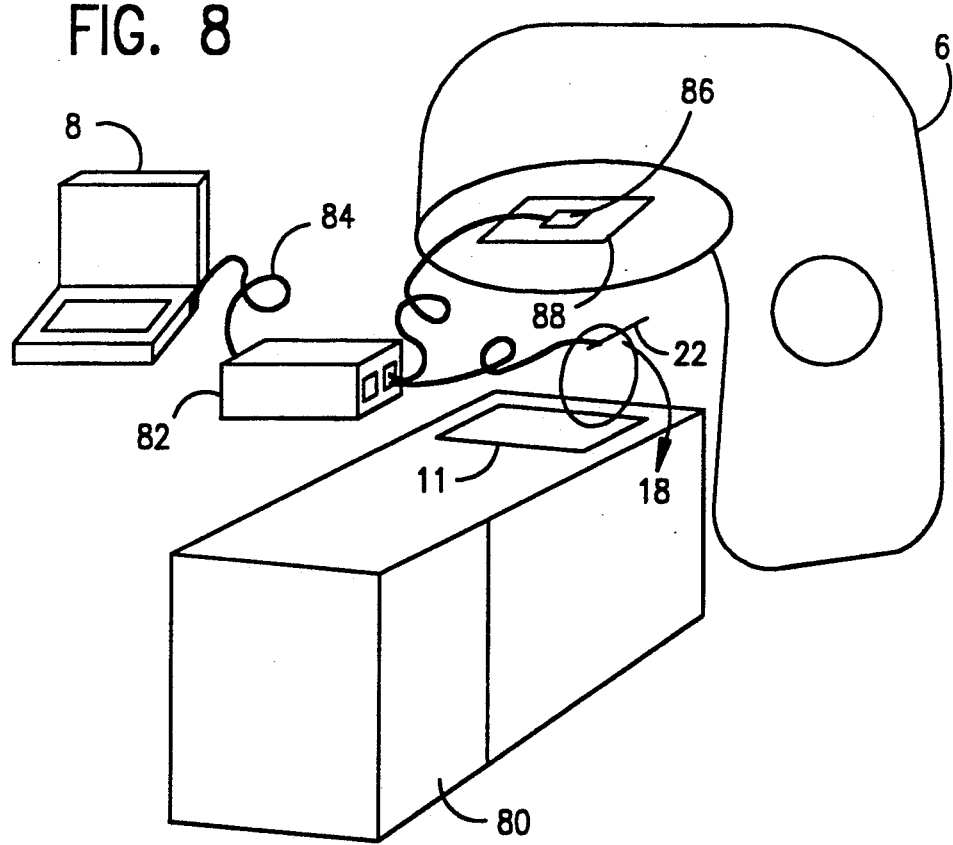
FIG. 8 is a drawing showing the interrelationship between the mechanical and computer systems which together form the treatment device portion of the computer controlled stereotaxic radiotherapy system of the present invention.

FIG. 8 illustrates the use of the instant inventive system during patient preparation for therapy treatment. The control computer (portable) 8 which has already received the patient data is connected by means of an RS 232 cable to the digitizer circuitry 82, which has been previously described. The digitizer circuitry 82 is connected both to the field source 86 and to the field sensor or probe 22. The field sensor 22 is mounted to the halo 18 which is itself secured to the base assembly 11 which is in turn secured to the treatment couch 80. The probe 22 is a six degree of freedom measuring device and reads the low frequency magnetic field generated by the field source 86. The position of the tip of the probe defines three coordinates (x, y, z) while the probe orientation defines three Euler space angles (azimuth, elevation, roll.) By means of the relationship between the probe 22 and the field source 86, the treatment machine 6 can be adjusted such that its beam strikes the center of the lesion to be treated. Alternatively, by means of the relationship between the probe 22 and the field source 86, a collision between the machine 6 and patient and/or supporting treatment couch 80 can be avoided by stopping the machine 6 or the motion of the couch 80.

The computer controlled stereotaxic radiotherapy system of the present invention operates as follows. Initially, either before or after surgery to remove the lesion, the patient is fitted with a halo 18 and connected halo support 16. The halo is attached to the patient's skull by means of the titanium screws 62. The patient is then placed on the couch of a CT scanner or MRI device which includes the base assembly 11 and the gyro assembly 24. The halo support 16 is affixed to the gyro assembly 24, thus fixing the head of the patient to the base assembly 11.

Before the patient is moved into the CT scanner 2 or MRI device, the stereotaxic coordinates phantom 20 is secured to the base 12. The phantom of the probe 22 is secured by means of the probe lock 66 to the halo 18, as previously described. The patient is then moved into the CT scanner 2 and a series of CT scans covering the entire volume of interest is performed. By means of the contrast material contained in the stereotaxic coordinates phantom 20, the CT scan of the lesion to be treated produces a definition of coordinates for the patient's skull. The contrast material produces a plurality of dots around the x-ray or CT scan of the patient's skull which contains the lesion. Thus, by turning the phantom image (data) a patient coordinate system is determined (origin, orientation) on the images. The stereotaxic coordinates of the lesion and the probe are determined as well on the pertinent images.

The images and lesion/probe coordinates produced on the CT scan 2 are transferred to the treatment planning computer 4. The treatment plan is then computed in a patient coordinate system previously determined by the phantom. The coordinates of the lesion and probe are shown on the plan, using the sensor of the aperture of the CT or MR scanner as the origin. From the phantom probe coordinates, the probe orientation (Euler angles) is determined. Now the probe position and its orientation in relation to the sensor of the lesion is known. Patient set-up for treatment can then proceed by first setting-up the probe 22 at the isocenter of the treatment machine 6, using the precomputed coordinates and angles, and then by moving the couch with the patient in a rectlinear manner by the difference between the x, y and z coordinates of the probe tip and the lesion center. Since the position of the treatment machine isocenter is now known from this treatment plan the stereotaxic lesion/probe coordinates are transferred from the patient CS into the treatment machine CS using the treatment machine isocenter as the origin.

It is important to note that the success of the present invention requires the diagnostic CT scan to be performed in the same position as the treatment is to be performed. It is for that reason that the same base assembly 11 structure is utilized with both the diagnostic machine 2 and the treatment machine 6.

The patient is then transferred to the couch 80 of the linear accelerator or treatment machine 6. The patient, still wearing the halo 18, is locked into the base assembly 11 and gyro assembly 24 which are setup—concerning x, (FIG. 4a) and y, (FIG. 5b) position, as well as elevation and azumith (FIG. 5d)—using the precomputed coordinates and angles from the treatment plan as already described.

The field source 86 is affixed to the head of the accelerator 6, as previously described. Using the field sensor 22, the isocenter of the linear accelerator 6 is defined as an origin of the magnetic field. Then, the treatment couch, together with the patient, is manipulated so that the x, y and z positions of the sensor 22, which are all within the low frequency magnetic field generated by the field source 86, are the same as prescribed by the stereotaxic coordinates of the sensor 22. These are the same coordinates which were originally determined by the planning computer 4 using the patient scans obtained from the CT scanner 2 with the field sensor 22 in place and subsequently transformed (mathematically) into treatment machine coordinate system. The isocenter of the treatment machine is used as an origin of the CS.

During the setup procedure, that is, during the couch and/or inventive system manipulation or motion, the sensor 22 readings of the magnetic field (namely the x, y and z and three Euler angles) are transferred in realtime to the portable computer 8, which is used for realtime monitoring of the sensor position and orientation within the field and which contains the three-dimensional digitizer software. When both the position and orientation are as prescribed, the patient is in the correct position for treatment. That is, the isocenter of the treatment plan generated by the planning computer 4 coincides with the isocenter of the linear accelerator 6 and the CS of the patient and treatment machine are in coincidence. Thus, the information transfer from the CT scanner 2 is accurately completed and the diagnostic, planning and treatment procedures are thus integrated.

Then, verification x-ray films may be taken in order to document that the tumor is properly covered by the radiation beam of the linear accelerator 6 and the patient is then treated. For all subsequent treatments, the patient is setup in the manner described above by using all six of the stereotaxic coordinates of the field sensor 22 as displayed on the portable computer 8. In addition to the x, y, and z coordinates of the lesion the three Euler angles—azumith, elevation and roll—are used.

The system of the present invention permits fractionated radiotherapy, that is, it permits a series of radiotherapy treatments to be given to a patient over time and, using the halo 18 which is affixed to the patient's skull for an extended period of time, such as 6-8 weeks, fractionated or single-fraction therapy can be provided to the patient in an accurate manner. As opposed to single-fraction treatment, fractionated treatment is suitable for brain tumors.

The three-dimensional digitizer system described herein can also be used for setting up the linear accelerator 6, or any other type of treatment machine, including diagnostic or operation room equipment. Such a three-dimensional digitizer system can also be used by itself, without the halo 18, in order to prevent a collision between the gantry of the linear accelerator and the patient couch.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. An integrated patient diagnostic and treatment system for intracranial lesions, comprising:
   a diagnostic device having a first treatment couch;
   a first positioning assembly secured to said first treatment couch, said first positioning assembly including a stereotaxic phantom assembly;
   a patient positioning device adapted to be attached to the skull of the patient and which is releasably secured to said first positioning assembly during the operation of said diagnostic device on said patient;
   a computer means for receiving output signals from said diagnostic device;
   a treatment system connected to said computer device, said treatment system including a second treatment couch;
   a second positioning assembly secured to said second treatment couch such that said patient positioning device may be releasably secured to said second treatment couch to perform treatment on said patient; and
   a magnetic positioner system having a component attached to said treatment system and a component attached to said patient positioning device, said magnetic positioner system being connected to said computer means;
   whereby said treatment device can be aligned such that it efficiently treats said intracranial lesion.

2. The patient diagnostic and treatment system of claim 1 wherein said second positioning assembly is movable in two different directions.

3. The patient diagnostic and treatment system of claim 1, wherein said magnetic positioner system measures the position of the lesion with respect to an x, y and z coordinate system.

4. The patient diagnostic and treatment system of claim 3, wherein said magnetic positioner system also measures the position of the lesion with respect to three Euler space angles.

5. The patient diagnostic and treatment system of claim 1, wherein said first and second positioning assemblies comprise a base support attached directly to said first and second treatment couches and a base movably attached thereto.

6. The patient diagnostic and treatment system of claim 5, further including a gyro assembly which forms part of said positioning assemblies and which is movably secured to said base to which said patient positioning device is releasably attached.

7. A method for providing integrated patient diagnosis and treatment for an intracranial lesion, comprising the steps of:
   fixing first and second identical positioning devices to treatment couches of diagnostic and treatment devices;
   fixing a patient positioning device to the skull of a patient;
   releasably securing said patient positioning device to said first positioning device;
   performing a diagnostic procedure with said diagnostic device on said patient to determine the position coordinates of said lesion within the skull of said patient;
   releasably securing said patient positioning device to said second positioning device;
   attaching different components of a three-dimensional magnetic positioner device to both said patient positioning device and said treatment device; and
   processing the position coordinates produced by said diagnostic procedure together with information generated by said three-dimensional magnetic positioner device to align an isocenter of said treatment device with said lesion for treatment.

8. The method of claim 7, further including the step of providing components for said first and second positioning devices which allow movement of said patient positioning device relative to said positioning devices.

9. The method of claim 8, wherein each of said first and second positioning devices are comprised of a base movably secured to a base support which is fixedly secured to said treatment couches.

10. The method of claim 9, wherein each of said first and second positioning devices are further comprised of a gyro assembly for releasably receiving said patient positioning device which gyro assembly is movably secured to said base.

11. The method of claim 7, wherein said step of fixing a patient positioning device to the skull of a patient includes using titanium screws to secure said device to the patient's skull.

12. The method of claim 7, further including the step of adjusting the position of said patient positioning device relative to said second positioning device in order to align isocenter of treatment device with said lesion.

13. The method of claim 7, wherein said three-dimensional magnetic positioner elements comprise a magnetic source attached to said treatment device and a magnetic field sensor attached to said patient positioning device.

14. The method of claim 7 wherein said three-dimensional magnetic positioner components provide the x, y and z coordinates of said lesion with respect to said isocenter of said treatment device.

15. The method of claim 14, wherein said three-dimensional magnetic positioner components further provide three Euler space angles of said lesion with respect to said isocenter of said treatment device.

16. The method of claim 7, wherein said processing step includes manipulating said patient and patient positioning device until one of said three-dimensional magnetic positioner components is positioned at the coordinates of said lesion as derived from the position coordinates determined during said diagnostic procedure.

17. The method of claim 7, wherein said processing step includes the real-time monitoring of the position of said three-dimensional magnetic positioner components.

18. The method of claim 7, wherein after said processing step, said lesion has its isocenter in correspondence with said isocenter of said treatment device.

* * * * *